(12) United States Patent
Schnider et al.

(10) Patent No.: US 9,546,136 B2
(45) Date of Patent: Jan. 17, 2017

(54) METHOD FOR PREPARATION OF IMIDODISULFURYL COMPOUNDS

(71) Applicant: LONZA LTD, Visp (CH)

(72) Inventors: Christian Schnider, Visp (CH); Dominique Roberge, Sierre (CH); Michael Gottsponer, Visperterminen (CH); Andreas Klein, Brig-Glis (CH); Thomas Gruetzner, Brig (CH); Michael Bittel, Visp (CH); Stefan Tille, Termen (CH); Anna-Christina Hormes, Visp (CH); Janine Leiggener, Visp (CH)

(73) Assignee: Lonza Ltd, Visp (CH)

( * ) Notice: Subject to any disclaimer, the term of this patent is extended or adjusted under 35 U.S.C. 154(b) by 0 days.

(21) Appl. No.: 14/397,605

(22) PCT Filed: Jul. 10, 2014

(86) PCT No.: PCT/EP2014/064785
§ 371 (c)(1),
(2) Date: Oct. 28, 2014

(87) PCT Pub. No.: WO2015/004220
PCT Pub. Date: Jan. 15, 2015

(65) Prior Publication Data
US 2016/0289177 A1 Oct. 6, 2016

Related U.S. Application Data

(60) Provisional application No. 61/844,963, filed on Jul. 11, 2013.

(30) Foreign Application Priority Data

Jul. 11, 2013 (EP) .................................. 13176189
Mar. 28, 2014 (EP) .................................. 14162217

(51) Int. Cl.
*C07C 303/36* (2006.01)
*C07C 311/48* (2006.01)

(52) U.S. Cl.
CPC .................................. *C07C 303/36* (2013.01)

(58) Field of Classification Search
CPC .... C07C 303/36; C07C 311/65; C07C 311/48; C07C 311/00
USPC ........................................... 564/82
See application file for complete search history.

(56) References Cited

U.S. PATENT DOCUMENTS

| 3,379,509 A | 4/1968 | Rolf |
| 2011/0034716 A1* | 2/2011 | Okumura ............... C07C 303/40 556/69 |
| 2012/0020867 A1* | 1/2012 | Morinaka ............. B01J 31/0252 423/386 |

FOREIGN PATENT DOCUMENTS

| CA | 710255 | 5/1965 |
| DE | 1143495 | 2/1963 |
| DE | 1159410 | 12/1963 |
| WO | WO 2009/123328 | 10/2009 |

OTHER PUBLICATIONS

Written Opinion and Search Report for PCT/EP2014/064785 (mailed—Sep. 23, 2014).

* cited by examiner

*Primary Examiner* — Rosalynd Keys
*Assistant Examiner* — Amy C Bonaparte
(74) *Attorney, Agent, or Firm* — Dority & Manning, P.A.

(57) ABSTRACT

The invention relates to a method for the preparation of imidodisulfuryl compounds in a continuous reaction at elevated temperatures.

30 Claims, No Drawings

METHOD FOR PREPARATION OF IMIDODISULFURYL COMPOUNDS

RELATED APPLICATIONS

This application is the national stage entry of International Patent Application No. PCT/EP2014/064785 having a filing date of Jul. 10, 2014, which claims the filing benefit of European Patent Application No. 13176189.2, having a filing date of Jul. 11, 2013, U.S. Provisional Patent Application No. 61/844,963, having filing date of Jul. 11, 2013, and European Patent Application No. 14162217.5, having a filing date of Mar. 28, 2014, all of which are incorporated herein by reference in their entirety.

The invention relates to a method for the preparation of imidodisulfuryl compounds in a continuous reaction at elevated temperatures.

BACKGROUND OF THE INVENTION

In the following text, if not otherwise stated, the following meanings are used:
CSI chlorosulfonyl isocyanate
CSOS chlorosulfonic acid
ClSI bis(chlorosulfonyl)-imide
FSI fluorosulfonyl isocyanate
FSOS fluorosulfonic acid
FR flow rate
RT room temperature Imidodisulfuryl compounds are used for a number of purposes. One example is the use of imidodisulfurylchlorid for the preparation of lithium bis(fluorosulfonyl)imid, which again is used as an electrolyte e.g. in lithium ionic batteries, which e,& can be used in automotive batteries, and is used as antistatic agent in touch screens.

DE 1 159 410 B discloses a method for preparation of halosulfonyl isocyanates by a reaction of halosulfonic acid with urea. The reaction is done preferably at a temperature of from 100 to 180° C. Specifically disclosed is the preparation of chlorosulfunyl isocyanate at a temperature of from 120 to 150° C.

DE 1 143 495 B discloses a method for preparation of imido-bis(sulfuryl)fluorid by a reaction of fluorosulfonic acid with urea. The reaction temperature is not stated apparently the reaction starts at room temperature and in the course of the reaction the reaction mixture is cooled from time to time.

CA 710255 A discloses a method for preparation of imido-bis(sulfurylchloride) by a reaction of chlorosulfonic acid with trichlorophosphazo-sulfuryl chloride. Methods such as disclosed in CA 710255 have the disadvantage of requiring phosphorus chemistry which is rather expensive and environmentally disadvantageous to use.

WO 20091123328 A1 discloses the preparation of ClSI in a batch method, details are given the example section of instant invention.

The reaction equation of instant invention for preparation of imidodisulfurylhalides, also named imidobis(sulfurylhalides), imidobissulfurylhalides or bis(halidosunnyl)imide, which also is applicable for similar compounds of instant invention, is depicted in Scheme 1;

Scheme 1

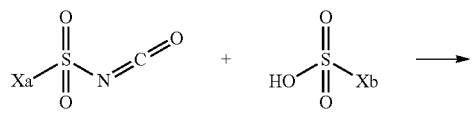

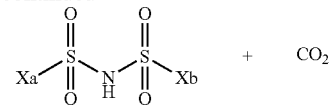

with Xa and Xb being halogen.

Both starting compounds, the isocyanate and the sulfonic acid, and the product, the his imide, are toxic and corrosive. In case of Xa and Xb being Cl, the product shows a very high exothermic decomposition at elevated temperatures, making it necessary to provide adequate safety measures in production. The heat of reaction deltaH is ca. 100 kJ/mol, the onset of decomposition of the imidosulfurylchloride is around 180° C. with an adiabatic temperature rise to temperatures well over 400° C. The reaction of CSI with FSOS and the reaction of PSI with CSOS show similar temperatures for the onset of decomposition.

Therefore the reaction temperature in batch processes in production is not higher than 150° C. to avoid the risk of explosion. The reaction times of the batch processes ranges from ca, 8 h to 24 h.

On the other hand the isocyanate and the sulfonic acid only react at elevated temperatures. Due to these circumstance and safety considerations, in the past the imidodisulfurylhalides have been prepared only in small batches and at temperatures well below the onset of decomposition as mentioned, leading to the mentioned long reaction times.

There was a need for a method for preparation of imidodisulfurylhalides, which does not need phosphorous chemistry, has short reaction times and high yields, where the product shows high purity, and allows for safe handling of the substances and of the reaction, also on a large scale.

Unexpectedly, it is possible to react a halosulfonyl isocyanate with a halosulfonic acid at temperatures above the onset temperature of decomposition of the reaction product, the imidosulfurylhalide without the expected decomposition of the desired imidodisulfurylhalide, the yields are high. It was unexpected to be able to conduct the reaction in a safe way. This allows for the desired short reaction times.

Furthermore the short reaction times can be realized still with a product with high purity, i.e. not showing discoloration due to decomposition or polymerization reactions usually taking place at too high temperatures.

SUMMARY OF THE INVENTION

Subject of the invention is a method for preparation of compound of formula (I);

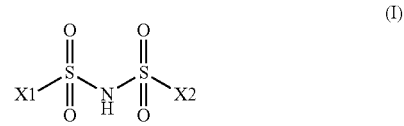

the method comprises three consecutive steps step (StepS1), step (StepS2) and step (StepS3); step (StepS1) comprises a reaction (ReacS1);
reaction (ReacS1) is a reaction of compound of formula (II) with compound of formula (III);

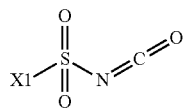

(II)

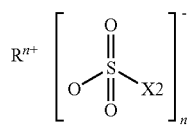

(III)

wherein
X1 and X2 are identical or different and independently from each other selected from the group consisting of F, Cl, Br, I, $C_{1-6}$ perfluoroalkyl, and tolyl;
$R^{n+}$ is selected from the group consisting of $H^+$, $Li^+$, $N^+$, $K^+$, $Mg^{2+}$, $Ca^{2+}$, $Zn^{2+}$, $Cu^{2+}$, $Al^{3+}$, $Ti^{3+}$, $Fe^{2+}$, $Fe^{3+}$, $B^{3+}$,

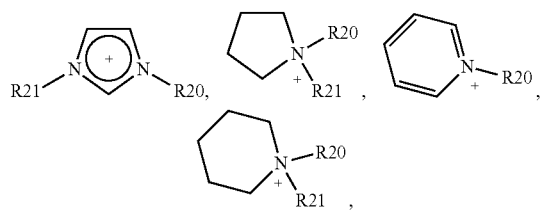

$[N(R20)(R21)(R22)R23]^+$, and $[P(R20)(R21)(R22)R23]^+$;
R20, R21, R22 and R23 are identical or different and independently from each other selected from the group consisting of H, $C_{1-8}$ alkyl, $C_{5-6}$ cycloalkyl, phenyl, benzyl, vinyl and allyl;
n is 1, 2 or 3,
the reaction (ReaeS1) is done in a continuous way;
in step (StepS1) a mixture of compound of formula (II) and compound of formula (III) passes through a device (DevS1), device (DevS1) is a continuously working device, in device (DevS1) the mixture of compound of formula (II) and compound of formula (III) is heated to a temperature (TempS1), temperature (TempS1) is of from 180 to 300° C., where the reaction (ReacS1) takes place, resulting in a reaction mixture,
in step (StepS2) the reaction mixture from device (DevS1) passes through a device (DevS2), device (DevS2) is a device for cooling the reaction mixture;
in step (StepS3) the reaction mixture from device (DevS2) passes through a device (DevS3), device (DevS3) is a device for back pressure regulation;
the reaction mixture is cooled to a temperature (TempS2) by the effects on the reaction mixture of device (DevS2) or of device (DevS3) or of a combination of device (DevS2) and device (DevS3), temperature (TempS2) is of from 0 to 150° C.

DETAILED DESCRIPTION OF THE INVENTION

Preferably, the method comprises furthermore a step (StepS4), which is done after step (StepS3), in step (StepS4) the reaction mixture from device (DevS3) passes through a device (DevS4) device (DevS4) is a device for separating $CO_2$ from the reaction mixture.
Preferably, X1 and X2 are identical and are selected from the group consisting of F, Cl, Br, $C_{1-6}$ perfluoroalkyl and tolyl;
more preferably, X1 and X2 are identical and are selected from the group consisting of F, Cl and $C_{1-6}$ perfluoroalkyl;
even more preferably, X1 and X2 are identical and are selected from the group consisting of F, Cl and $CF_3$;
especially, X1 and X2 are identical and are Cl or $CF_3$;
more especially, X1 and X2 are Cl.
Preferably,
$R^{n+}$ is selected from the group consisting of $H^+$, $Li^+$, $Na^+$, $K^+$,

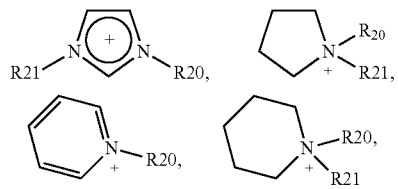

$[N(R20)(R21)(R22)(R23)]^+$;
R20, R21, R22 and R23 are identical or different and independently from each other selected from the group consisting of H, $C_{1-8}$ alkyl, $C_{5-6}$ cycloalkyl, phenyl, benzyl, vinyl and allyl;
more preferably,
$R^{n+}$ is selected from the group consisting of $H^+$, $Li^+$, $Na^+$, $K^+$,

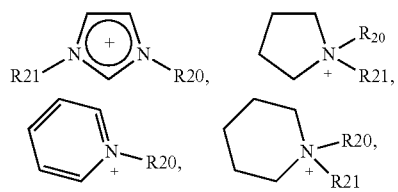

$[N(R20)(R21)(R22)R23]^+$;
R20, R21, R22 and R23 are identical or different and independently from each other selected from the group consisting of H, $C_{1-8}$ alkyl, $C_{5-6}$ cycloalkyl, phenyl and benzyl;
even more preferably,
$R^{n+}$ is selected from the group consisting of $H^+$, $Li^+$, $Na^+$, $K^+$,

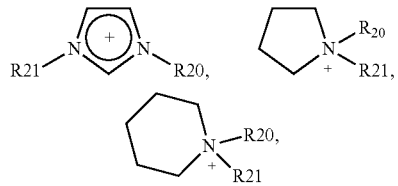

$[N(R20)(R21)(R22)R23]^+$;
R20, R21, R22 and R23 are identical or different and independently from each other selected from the group consisting of H, $C_{1-8}$ alkyl, $C_{5-6}$ cycloalkyl, phenyl and benzyl;

especially,
R"+ is selected from the group consisting of H+, Li+, Na+, K+,

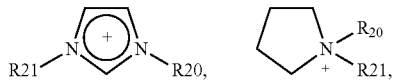

[N(R20)(R21)(R22)R23]+;
R20, R21, R22 and R23 are identical or different and independently from each other selected from the group consisting of H, $C_{1-8}$ alkyl, $C_{5-6}$ cycloalkyl, phenyl and benzyl,
more especially,
R"+ is selected from the group consisting of H+, Na+, K+ and

and
R20 and R21 are identical or different and independently from each other selected from the group consisting of H and $C_{1-8}$ alkyl;
even more especially,
R"+ is selected from the group consisting of H+, Na+ and

and
R20 and R21 are identical or different and independently from each $C_{1-8}$ alkyl;
in particular,
R"+ is H+ or

and
R20 and R21 are identical or different and independently from each $C_{1-4}$ alkyl;
more in particular,
R"+ is H+ or

and
R20 and R21 are identical or different and independently from each selected from the group consisting of methyl, ethyl and n-butyl.
When R"+ is H+ then compound of formula (III) can also displayed in the conventional way, that is as compound of formula (IIIconv).

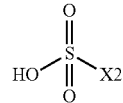

(IIIconv)

Preferably, the reaction (ReacS1) is done in a tubular reactor. During the passage through device (DevS1), the initially fed mixture gradually is converted to the reaction mixture by the reaction.

Preferably, device (DevS1) is selected from the group consisting of tube, microreactor, shell and tube heat exchanger, plate heat exchanger and any common device which purpose is to exchange heat from a mixture;
more preferably it is a tube;
even more preferably it is a coiled tube.

Preferably, device (DevS2) is selected from the group consisting of tube, microreactor, shell and tube heat exchanger, plate heat exchanger and any common device which purpose is to exchange heat from a reaction mixture;
more preferably it is a tube;
even more preferably it is a coiled tube.

Especially, device (DevS1) and device (DevS2) are coiled tubes.

Preferably, device (DevS3) is a conventional back pressure regulating device.

Preferably, device (DevS4) a device capable of separating gaseous $CO_2$ from a liquid, any known device suitable for this purpose for can be used for this purpose, more preferably device (DevS4) is a column or a cyclone.

The heating in device (DevS1) can be done be any known means, preferably it is done by electric heating or by heating with a fluid heat carrier.

Cooling in device (DevS2) can be clone be any known means, preferably it is done by a fluid cooling medium.

Depending on the scale of the reaction and thereby on the scale of the apparatus, wherein the method is done, the cooling of the reaction mixture is done not only by the effect on the reaction mixture of device (DevS2), i.e. during the passage of the reaction mixture through device (DevS2), but additionally the effects on the reaction mixture of device (DevS3), i.e. the passage through device (DevS3) contributes to the cooling. This is especially the case when the scale of the reaction is rather small, e.g. when the method is done on lab scale, whereas in case where the method is done on a production scale the cooling will usually primarily be done during the passage through device (DevS2).

In another embodiment, especially on production scale, cooling can also be achieved by the expansion and pressure release affected by device (DevS3).

Also a combination of cooling during the passage through device (DevS2) with a cooling by expansion affected by device (DevS3) is possible.

Preferably, heating in device (DevS1) and cooling in Device (DevS2) is realized in form of a tube-in-tube set up, in form of a tube-in-container set up, in form of a shell and tube heat exchanger, plate heat exchanger or any common device which purpose is to exchange heat from a mixture or a reaction mixture;
more preferably, heating in device (DevS1) and cooling in Device (DevS2) is realized in form of a tube-in-tube set up or in form of a tube-in-container set up.

Reaction (ReacS1) is triggered in device (DevS1) by the heating of the mixture in the device (DevS1) to the temperature (TempS1).

Reaction (ReacS1) is quenched in device (DevS2), this is done by the cooling the reaction mixture in the device (DevS2) to the temperature (TempS2).

Preferably, temperature (TempS1) is of from 190 to 280° C., more preferably of from 200 to 260° C., even more preferably from 210 to 255° C., especially from 220 to 255° C.

Preferably, temperature (TempS2) is from 10 to 120° C. more preferably from 15 to 100° C., even more preferably from 15 to 90° C., especially from 15 to 85° C., more especially from 20 to 85° C.

The melting point of pure ClSI is ca. 35° C., therefore the lowest possible value of temperature (TempS2) is governed by the conversion of the reaction, since residual compound of formula (II) and residual compound of formula (III) in the reaction mixture naturally lowers the melting point of the reaction mixture after the reaction and allows for lower values of temperature (TempS2).

Reaction (ReacS1) is done at a pressure (PressS1). Preferably, pressure (PressS1) is from 10 to 1000 bar, more preferably from 20 to 600 bar, even more preferably from 50 to 500 bar, especially from 60 to 400 bar, more especially from 65 to 300 bar, even more from 65 to 200 bar, in particular from 65 to 150 bar.

The pressure (PressS1) in device (DevS1) and device (DevS2) is controlled and held by the device (DevS3).

Time (TimeS1) is the time, where the mixture is exposed to heating and to the temperature (TempS1) in device (DevS1). During time (TimeS1) the reaction (ReacS1) takes place. Time (TimeS1) is therefore a residence time and is preferably the residence time of the mixture in device (DevS1).

Preferably, time (TimeS1) is from 0.5 sec to 4 h, more preferably from 1 sec to 2 h, even more preferably 1 mm, to 1 h, especially from 2 min to 30 min, more especially from 2 min to 20 min, even more especially from 3 min to 17 min.

Time (TimeS2) is the time, where the reaction mixture is cooled to temperature (TempS2). The cooling can be done by the action of device (DevS2), by the action of device (DevS3) or by the action of device (DevS2) and device (DevS3). The cooling quenches the reaction, Time (TimeS2) is therefore a residence time and is preferably the residence time of the reaction mixture in device (DevS2) and in device (DevS3).

Preferably, time (TimeS2) is from 0.1 sec to 2 h, more preferably from 0.5 sec to 1 h, even more preferably 1 sec to 30 min, especially from 10 sec to 30 min, more especially from 25 sec to 25 min, even more especially from 1 min to 25 min.

Preferably, Time (TimeS2) is from 0.0001 to 0.5 fold of time, more preferably from 0.001 to 0.3 fold, of time (TimeS1).

Preferably, the molar amount of compound of formula (III) is from 0.5 to 1.5 fold, more preferably from 0.75 to 1.25 fold, even more preferably from 0.85 to 1.15 fold, of the molar amount of compound of formula (II).

Compound of formula (II) and compound of formula (III) can be fed into the device (DevS1) as a premixed mixture or can be fed into the device (DevS1) separately and are mixed in device (DevS1), For the purpose of mixing before or in device (DevS1) any suitable installation for mixing can be used, which are known in the state of the art, such as a common branch connection, e.g. a T or Y piece, or a static mixing device.

Preferably the heating to temperature (TempS1) in device (DevS1) is done only after compound of formula (II) and compound of formula (HI) are present as a mixture in device (DevS1.).

The feeding of compound of formula (II) and compound of formula (III), either separately or in form of a mixture, is done by a device (DevS0).

Device (DevS0) is a pressuring device conventionally used to convey a fluid against pressure, such as a pump. When compound of formula (II) and compound of formula (III) are fed separately into device (DevS1), then preferably device (DevS0) has for each compound a respective device.

Preferably, device (DevS1) and device (DevS2) are during operation in permanent fluid connection with each other and are both under pressure (PressS1).

Preferably, device (DevS0) is the device that builds up the pressure (PressS1) in device (DevS1) and in the device (DevS2) against the device (DevS3), which is necessary to carry out the reaction (ReacS1) at the temperature (TempS1).

More preferably, compound of formula (II) and compound of formula (III) are mixed under ambient pressure and at ambient temperature and then are fed into device (DevS1).

In case of device (DevS1) and/or device (DevS2) being tubes, especially coiled tubes, due to constructional limitations or due to density fluctuations and the like hot spots or cold spots can occur in spite of efforts to avoid them. Therefore any mentioned temperatures are meant to be average temperatures in view of possible hot or cold spots.

Conventional back pressure regulating devices, which can be used for device (DevS3), work discontinually, i.e. by opening and closing they release the product stream while holding the pressure. This leads naturally to variations in the pressure. Therefore the pressure (PressS1) is meant to be an average pressure.

All parts in contact with the mixture of compound of formula (II) and compound of formula (III) and with the reaction mixture are made out of respective materials, which are resistant to the attack of the chemicals under the respective conditions, i.e. stainless steel, hastelloy, such as hastelloy B or hastelloy C, titanium, tantalum, silicon carbide, silicon nitride etc., they can also be passivized or lined with material inert to the chemicals, such as PTFE.

Compound of formula (I) can be used from device (DevS4) for any subsequent reaction without further purification, in case of a further purification, preferably, the liquid phase obtained from device (DevS4) is further purified by removing any low boiling residues, preferably this is done by using a film evaporator, more preferably a wiped film evaporator.

EXAMPLES conv conversion was determined by measuring the content (CONT-CSI) of CSI by weight-% after reaction in the reaction mixture with IR spectroscopy against a standard, conv is [100−content (CONT-CSI)] in %.
FR flow rate
nd not determined
p1 pressure (PressS1)
t1 time (TimeS1)
t2 time (TimeS2)
T1 temperature (TempS1)
T2 temperature (TempS2)

Examples 1 to 14

In the examples an equimolar premix of CSOS and CSI was fed into device (DevS1).

The examples were carried out with
device (DevS0): piston pump 260D from ISCO Teledyne
device (DevS1) being a ⅛ inch coiled tube with internal volume VolS1 made of hastelloy C. For the heating a coiled-tube-in-container set up was used. Heating medium was conventional oil.

device Dev(S2) being a ⅛ inch tube with ca. 1.5 mL internal volume made of hastelloy C. Cooling was done by simply contact of the tube with the air of the room having room temperature.
device (DevS3): standard back pressure regulator from Swagelok of KPB Series
device (DevS4): the $CO_2$ was separated from the reaction mixture in an open gas flask The obtained ClSI in each example was a colorless to yellow liquid.

The structure was confirmed by IR spectroscopy:
IR (ATR, 24 scans, v in cm-1): 3205 (m), 2758 (w), 2652 (w), 1727 (w) 1416 (s), 1318 (m), 1273 (w), 1206 (m), 1167 (s), 862 (s), 567 (s), 500 (s)

| Ex | VolS1 ml | FR [g/min] | T1 [° C.] | t1 [min] | T2 [° C.] | t2 [min] | p1 [bar] | conv [%] |
|---|---|---|---|---|---|---|---|---|
| 1 | 5.7 | 1.70 | 240 | 5.6 | RT | 1.4 | 77 | 95.8 |
| 2 | 5.7 | 1.70 | 240 | 5.6 | RT | 1.4 | 79 | 94.4 |
| 3 | 5.7 | 1.52 | 230 | 6.3 | RT | 1.5 | 87 | 92.5 |
| 4 | 5.7 | 1.52 | 230 | 6.3 | RT | 1.5 | 77 | 92.6 |
| 5 | 5.7 | 1.52 | 230 | 6.3 | RT | 1.5 | 84 | 92.4 |
| 6 | 5.14 | 0.58 | 200 | 15.5 | RT | 1 | 81 | 65.8 |
| 7 | 5.14 | 0.87 | 210 | 10.3 | RT | 1 | 82 | 60 |
| 8 | 5.14 | 0.58 | 210 | 15.5 | RT | 1 | 82 | 79.8 |
| 9 | 5.14 | 0.87 | 220 | 10 | RT | 1 | 88 | 83.3 |
| 10 | 5.14 | 0.58 | 220 | 15 | RT | 1 | 80 | 90.5 |
| 11 | 5.14 | 1.74 | 230 | 5 | RT | 1.5 | 81 | 62.5 |
| 12 | 5.14 | 4.4 | 250 | 2.0 | RT | 0.5 | 85 | 73.6 |
| 13 | 5.14 | 2.2 | 250 | 3.9 | RT | 1 | 86 | 93.5 |
| 14 | 5.14 | 1.15 | 250 | 7.5 | RT | 1.5 | 87 | 97.5 |

Examples 15 to 17

In the examples CSOS and CSI was fed separately into device (DevS1) and were mixed in device (DevS1) by a inline static mixing device.

The examples were carried out with
device (DevS0): piston pump 260D from ISCO Teledyne
device (DevS1) being a ⅛ inch coiled tube with internal volume VolS1 made of hastelloy C. For the heating a coiled-tube-in-container set up was used. Heating medium was conventional oil.
device Dev(S2) being a ⅛ inch tube with ca. 1.5 mL internal volume made of hastelloy C. Cooling was done by simply contact of the tube with the air of the room having room temperature.
device (DevS3): standard back pressure regulator from Swagelok of KPB Series
device (DevS4): the $CO_2$ was separated from the reaction mixture in an open glas flask The obtained ClSI in each example was a colorless to yellow liquid.

The structure was confirmed by IR spectroscopy, the data is given in the description of example 1 to 14.

| Ex | molar ratio CSOS:CSI | VolS1 ml | FR [g/min] | T1 [° C.] | t1 [min] | T2 [° C.] | t2 [min] | p1 [bar] | conv [%] |
|---|---|---|---|---|---|---|---|---|---|
| 15 | 0.95 | 5.7 | 1.52 | 240 | 6.3 | RT | 1.5 | 80 | 95 |
| 16 | 0.95 | 6.8 | 2.23 | 240 | 5.1 | RT | 1 | 82 | 94.6 |
| 17 | 1.06 | 6.8 | 2.35 | 240 | 4.9 | RT | 1 | 84 | 88.4 |

Examples 18 to 21

In the examples an equimolar premix of CSOS and CSI was fed into device (DevS1).

The examples were carried out with
device (DevS0): piston pump 260D from ISCO Teledyne
device (DevS1) being a ¼ inch coiled tube with ca. 54 ml internal volume made of hastelloy C. For the heating a coiled-tube-in-container set up was used. Heating medium was conventional oil.
device Dev(S2) being a ⅛ inch tube with ca. 15 gal, internal volume made of hastelloy C. Cooling was done by simply contact of the time with water at different temperature levels T2
device (DevS3): standard back pressure regulator from Swagelok of KPB Series
device (DevS4): the $CO_2$ was separated from the reaction mixture in an open glas flask The obtained ClSI in each example was a colorless to yellow liquid.

The structure was confirmed by IR spectroscopy, the data is given in the description of example 1 to 14.

| Ex | FR [g/min] | T1 [° C.] | t1 [min] | T2 [° C.] | t2 [min] | p1 [bar] | conv [%] |
|---|---|---|---|---|---|---|---|
| 18 | 25 | 240 | 3.6 | 20 | 1 | 72 | 87.1 |
| 19 | 16.5 | 240 | 5.5 | 20 | 1 | 88 | 94.5 |
| 20 | 17 | 230 | 5.3 | 80 | 1 | 83 | 91.7 |
| 21 | 14.3 | 230 | 6.4 | 80 | 1 | 84 | 90.6 |

Comparative Example

Due to the onset of decomposition it is not allowed to do a batch reaction at a temperature of higher than 160° C. for comparison with the continuous reaction of instant invention. The risk of explosion is too high. Therefore only batch reactions at 150° C. are allowed due to these safety restrictions.

An equimolar amount of CSI was added to CSOS at 120° C. over 3 h, then the mixture was heated in 3 h to 150° C. and stirred at 150° C. for 7 h. Conversion was only 90%. Therefore total reaction time to reach 90% conversion was 13 h. The color was yellow.

A color which is darker than yellow must be avoided under all circumstances in the batch process since it is an indication of a substantial amount of decomposition which again is an indication of an explosure being very close.

WO 2009/123328 A1 discloses in Synthesis Example 2 the preparation of ClSI in a batch method. During 2 h CSI was added to CSOS at 120° C. then the mixture was stirred for 6 h at 150° C. Yield was 65.6%.

Example 22

An equimolar premix of CSOS and CSI was fed into device (DevS1).

The example was carried out with
device (DevS0): commercially available piston pump
a device (DevS1) being a ½ inch coiled tube with ca, 1200 ml internal volume made of hastelloy C. For the heating jacket heating was used. Heating medium was conventional oil.
device Dev(S2) being a ¼ inch tube with ca. 200 mL internal volume made of hastelloy C. For the cooling jacket cooling was used. Cooling medium was conventional oil.
device (DevS3): commercially available standard back pressure regulator was used.
device (DevS41): the $CO_2$ was separated in a standard separating device The obtained ClSI was a colorless to yellow liquid.
The structure was confirmed by IR spectroscopy, the data is given in the description of example 1 to 14.

| Ex | FR [kg/h] | T1 [° C.] | t1 [min] | T2 [° C.] | t2 [sec] | p1 [bar] | conv [%] |
|---|---|---|---|---|---|---|---|
| 22 | 22.8 | ca. 230 | 5.3 | ca. 50 | ca. 30 | 80 | 96.5 |

Example 23

An equimolar premix of triflouro methane sulfonic acid and CSI was fed into device (DevS1).

The example was carried out with
device (DevS0): piston pump 260D from ISCO Teledyne
device (DevS1) being a ⅛ inch coiled tube with internal volume VoIS1 made of hastelloy C. For the heating a jacket heating set up was used, heating medium was conventional oil.
device Dev(S2) being a ⅛ inch tube with ca. 1.5 mL internal volume made of hastelloy C. Cooling was done by simple contact of the tube with the air of the room having room temperature.
device (DevS3): standard back pressure regulator from Swagelok of KPB Series
device (DevS4): the $CO_2$ was separated from the reaction mixture in an open glas flask.

The obtained compound of formula (I) was a colorless to yellow liquid.

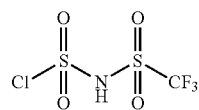

(1)

| Ex | VoIS1 ml | FR [g/min] | T1 [° C.] | t1 [min] | T2 [° C.] | t2 [min] | p1 [bar] | conv [%] |
|---|---|---|---|---|---|---|---|---|
| 23 | 10 | 4 | 230 | 3.2 | RT | ca. 1 | 80.4 | 90.8 |

The structure was confirmed by IR and NMR spectroscopy:
IR (ATR, 24 scans, v in cm-1): 3279 (w), 1399 (s) 1357 (s): 1176 (s) 1149 (s), 740 (s), 611 (s), 581 (s), 510 (s) 549 (s), 476 (s).
NMR (CD3CN, 400 MHz, 24° C., ref. 1,4 difluorobenzene) δ=−7835 ppm Furthermore the formation of the desired product by the reaction was confirmed by comparison of the heat of formation obtained by DSC measurements and high level calculated data.

| Method | ΔH in J/g | ΔH° R in KJ/mol |
|---|---|---|
| DSC | Average value 322 J/g | 64 kJ/mol |
| Turbomole/Gaussian | | 62 kJ/mol |

DSC was measured dynamically with a heat rate of 0.4° C./min.
Turbomole: Quantum mechanical calculations were done with the program TURBOMOLE, V6.5 (18161), Ahlrichs, M. Baer, M. Haeser, H. Horn, and C. Koelmel, Electronic structure calculations on workstation computers: the program system TURBOMOLE, Chem. Phys. Lett. 162: 165 (1989); and
Gaussian: Gaussian 09, Revision D.01, M. J. Frisch, G. W. Trucks, H. B. Schlegel, G. E. Scuseria, M. A. Robb, J. R. Cheeseman, G. Scalmani, V. Barone, B. Mennucci, G. A. Petersson, H. Nakatsuji, M. Caricato, X. Li, H. P. Hratchian, A. F. Izmaylov, J. Bloino, G. Zheng, J. L. Sonnenberg, M. Hada, M. Ehara, K. Toyota, R. Fukuda, J. Hasegawa, M. Ishida, T. Nakajima, Y. Honda, O. Kitao, H. Nakai, T. Vreven, J. A. Montgomery, Jr., J. E. Peralta, F. Ogliaro, M. Bearpark, J. J. Heyd, E. Brothers, K. N. Kudin, V. N. Staroverov, R. Kobayashi, J. Normand, K. Raghavachari, A. Rendell, J. C. Burant, S. S. Iyengar, J. Tomasi, M. Cossi, Rega, J. M. Millam, M. Klene, J. E. Knox, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, R. L. Martin, K. Morokuma, V. G. Zakrzewski, G. A. Voth, P. Salvador, J. J. Dannenberg, S. Dapprich, A. D. Daniels, Ö. Farkas, J. B. Forssman, J. V. Ortiz, J. Cioslowski, and D. J. Fox, Gaussian, Inc., Wallingford Conn., 2009;
using the method B3LYP 6-31G.

Examples 24 and 25

An equimolar premix of flouro sulfonic acid and CSI was fed into device (DevS1).

The examples were carried out with
device (DevS0): piston pump 260D from ISCO Teledyne
device (DevS1) being a ⅛ inch coiled tube with internal volume VoIS1 made of hastelloy C. For the heating a jacket heating set up was used, heating medium was conventional oil.
device Dev(S2) being a ⅛ inch tube with ca. 1.5 internal volume made of hastelloy C. Cooling was done by simple contact of the tube with the air of the room having room temperature.
device (DevS3): standard back pressure regulator from Swagelok of KPB Series
device (DevS4): the $CO_2$ was separated from the reaction mixture in an open gas flask The obtained compound of formula (2) was a colorless to yellow liquid.

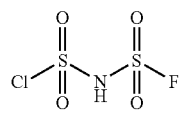
(2)

| Ex | VolS1 ml | FR [g/min] | T1 [° C.] | t1 [min] | T2 [° C.] | t2 [min] | p1 [bar] | conv [%] |
|---|---|---|---|---|---|---|---|---|
| 24 | 10 | 2.4 | 230 | 6.6 | RT | ca. 1 | 83.7 | 68.7 |
| 25 | 10 | 5.1 | 230 | 3.1 | RT | ca. 1 | 83.7 | 57.4 |

The structure was confirmed by NMR spectroscopy:

NMR (CD3CN, 400 MHz, 24° C., ref: benzenesulfonyl fluoride) δ=57.24 ppm

Application Example

The purity and yield of any of the examples 1 to 2.2 can be determined indirectly by using the respective obtained product as substrate in a reaction for the preparation of bis(fluorosulfonyl)-imide. As example for such determination of yield and purity in the following is described how the product prepared according to example 22 was used as substrate for the preparation of bis[di((fluorosulfonyl)imide] zinc salt in analogy to Synthesis Example 19-1 of WO 2009/123328 A1:

In a 500 ml reaction vessel, 179.3 g valeronitrile and 20.3 g ClSI (0.093 mol, prepared according to example 22) were charged, followed by stirring. Into the reaction vessel, 10.6 g (0.10 mol) of anhydrous $ZnF_2$ were added, followed by conducting a reaction at room temperature (25° C.) for 3 hours. The bis[di(fluorosulfonyl)imide]zinc salt was obtained as solution (yield 66.4%, determined by $^{19}F$-NMR and calculated based on ClSI (of a content of 100%)).

Any of the products prepared according to examples 1 to 22 of instant invention had a similar purity and was obtained in similar yield.

Example 26

An equimolar premix of 1-n-butyl-3-methylimidazolium trifluoromethanesulfonate and CSI was fed into device (DevS1).

The example was carried out with device (DevS0): piston pump 260D from ISCO Teledyne device (DevS1) being a ⅛ inch coiled tube with internal volume VolS1 made of hastelloy C. For the heating a jacket heating set up was used, heating medium was conventional oil.

device Dev(S2) being a ⅛ inch tube with ca. 1.5 mL internal volume made of hastelloy C. Cooling was done by simple contact of the tube with the air of the room having room temperature.

device (DevS3): standard back pressure regulator from Swagelok of KPB Series device (DevS4): the $CO_2$ was separated from the reaction mixture in an open glas flask The obtained compound of formula (I) was a yellow liquid

| Ex | VolS1 ml | FR [g/min] | T1 [° C.] | t1 [min] | T2 [° C.] | t2 [min] | p1 [bar] | conv [%] |
|---|---|---|---|---|---|---|---|---|
| 26 | 5 | 0.51 | 180 | 0.8 | RT | ca. 1 | 80 | 87 |

For the reaction product the following analytical data was measured.

IR (ATR, 24 scans, v in cm-1): 3122 (w), 2966 (w), 1573 (w), 1404 (w), 1353 (w) 1256 (s), 1224(m), 1156 (s), 1029 (s), 836 (m), 746 (m), 636 (s), 622 (s), 584 (s) 574 (s)

NMR (CD3CN, 400 MHz, 24° C., ref. 1,4 difluorobenzene) δ=−79.28 ppm

The invention claimed is:
1. A method for the preparation of a compound of formula (I);

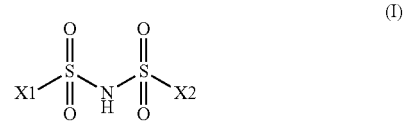
(I)

the method comprising three consecutive steps comprising a step (StepS1), a step (StepS2) and a step (StepS3);
the step (StepS1) comprising a reaction (ReacS1);
wherein the reaction (ReacS1) is a reaction of a compound of formula (II) with a compound of formula (III);

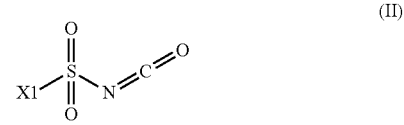
(II)

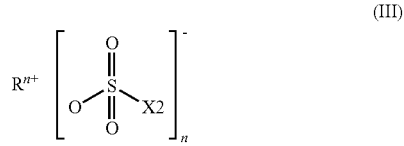
(III)

wherein
X1 and X2 are identical or different and X1 and X2 are independently from each other selected from the group consisting of F, Cl, Br, I, $C_{1-6}$ perfluoroalkyl, and tolyl;
$R^{n+}$ is selected from the group consisting of $H^+$, $Li^+$, $Na^+$, $K^+$, $Mg^{2+}$, $Ca^{2+}$, $Zn^{2+}$, $Cu^{2+}$, $Al^{3+}$, $Ti^{3+}$, $Fe^{2+}$, $Fe^{3+}$, $B^{3+}$,

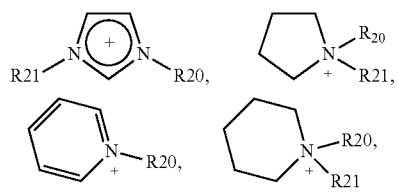

$[N(R20)(R21)(R22)R23]^+$, and $[P(R20)(R21)(R22)R23]^+$;
R20, R21, R22 and R23 are identical or different and R20, R21, R22 and R23 are independently from each other selected from the group consisting of H, $C_{1-8}$ alkyl, $C_{5-6}$ cycloalkyl, phenyl, benzyl, vinyl and ally; and n is 1, 2 or 3;

wherein the reaction (ReacS1) is continuous;

wherein in the step (StepS1) a mixture of the compound of formula (II) and the compound of formula (III) passes through a device (DevS1), wherein the device (DevS1) is a continuously working device, and in the device (DevS1) the mixture of the compound of formula (II) and the compound of formula (III) is heated to a temperature (TempS1) of from 180 to 300° C. where the reaction (ReacS1) takes place, resulting in a reaction mixture, wherein in step (StepS2) the reaction mixture from the device (DevS1) passes through a device (DevS2), wherein the device (DevS2) is a device for cooling the reaction mixture;

wherein in step (StepS3) the reaction mixture from the device (DevS2) passes through a device (DevS3), wherein the device (DevS3) is a device for back pressure regulation;

wherein the reaction mixture is cooled to a temperature (TempS2) of from 0 to 150° C. by the device (DevS2), the device (DevS3), or a combination thereof.

2. The method according to claim 1, wherein the method further comprises a step (StepS4), which is done after the step (StepS3), wherein in the step (StepS4) the reaction mixture from the device (DevS3) passes through a device (DevS4), wherein the device (DevS4) is a device for separating $CO_2$ from the reaction mixture.

3. The method according to claim 1, wherein
X1 and X2 are identical and are selected from the group consisting of F, Cl, Br, $C_{1-6}$ perfluoroalkyl and tolyl.

4. The method according to claim 1, wherein
$R^{n+}$ is selected from the group consisting of $H^+$, $Li^+$, $Na^+$, $K^+$,

[structures: imidazolium, pyrrolidinium, pyridinium, piperidinium cations with R20, R21]

and $[N(R20)(R21)(R22)R23]^+$;

R20, R21, R22 and R23 are identical or different and R20, R21, R22 and R23 are independently from each other selected from the group consisting of H, $C_{1-8}$ alkyl, $C_{5-6}$ cycloalkyl, phenyl, benzyl, vinyl and allyl.

5. The method according to claim 1, wherein
the device (DevS1) is selected from the group consisting of a tube, a microreactor, a shell and tube heat exchanger, a plate heat exchanger and any device that can exchange heat from a reaction mixture.

6. The method according to claim 1, wherein
the device (DevS2) is selected from the group consisting of a tube, a microreactor, a shell and tube heat exchanger, a plate heat exchanger and any device that can exchange heat from a reaction mixture.

7. The method according to claim 1, wherein
the device (DevS3) is a back pressure regulating device.

8. The method according to claim 1, wherein
the temperature (TempS1) is from 190 to 280° C.

9. The method according to claim 1, wherein
the temperature (TempS2) is from 10 to 120° C.

10. The method according to claim 1, wherein
the reaction (ReacS1) is done at a pressure (PressS1) of from 10 to 1000 bar.

11. The method according to claim 1, wherein
a time (TimeS1) that the mixture is exposed to heating at the temperature (TempS1) in the device (DevS1) is from 0.5 sec to 4 h.

12. The method according to claim 1, wherein
a time (TimeS2) that the mixture is cooled to the temperature (TempS2) is from 0.1 sec to 2 h.

13. The method according to claim 1, wherein
the ratio of the molar amount of the compound of formula (III) to the molar amount of the compound of formula (II) is from 0.5:1 to 1.5:1.

14. A method for the preparation of a compound of formula (I);

$$X1-\underset{\underset{O}{\|}}{\overset{\overset{O}{\|}}{S}}-\underset{H}{N}-\underset{\underset{O}{\|}}{\overset{\overset{O}{\|}}{S}}-X2 \quad (I)$$

the method comprising a reaction (ReacS1);

wherein the reaction (ReacS1) is a reaction of a compound of formula (II) with a compound of formula (III) at a temperature (TempS1) of from 180 to 300° C.;

$$X1-\underset{\underset{O}{\|}}{\overset{\overset{O}{\|}}{S}}-N=C=O \quad (II)$$

$$R^{n+}\left[\underset{\underset{O}{\|}}{\overset{\overset{O}{\|}}{O-S-X2}}\right]_n^- \quad (III)$$

wherein
X1 and X2 are identical or different and X1 and X2 are independently from each other selected from the group consisting of F, Cl, Br, I, $C_{1-6}$ perfluoroalkyl, and tolyl;

$R^{n+}$ is selected from the group consisting of $H^+$, $Li^+$, $Na^+$, $K^+$, $Mg^{2+}$, $Ca^{2+}$, $Zn^{2+}$, $Cu^{2+}$, $Al^{3+}$, $Ti^{3+}$, $Fe^{2+}$, $Fe^{3+}$, $B^{3+}$,

[structures: imidazolium, pyrrolidinium, pyridinium, piperidinium cations with R20, R21]

[N(R20)(R21)(R22)R23]$^+$, and [P(R20)(R21)(R22)R23]$^+$;
R20, R21, R22 and R23 are identical or different and R20, R21, R22 and R23 are independently from each other selected from the group consisting of H, $C_{1-8}$alkyl, $C_{5-6}$ cycloalkyl, phenyl, benzyl, vinyl and allyl; and
n is 1, 2 or 3;
wherein the reaction (ReacS1) continuous, and
wherein the reaction (ReacS1) is done at a pressure (PressS1) of from 10 to 1000 bar.

15. The method according to claim 14, wherein
the method comprises three consecutive steps comprising a step (StepS1), a step (StepS2) and a step (StepS3);
the step (StepS1) comprising the reaction (ReacS1) as defined in claim 14;
wherein in the step (StepS1) a mixture of the compound of formula (II) and the compound of formula (III) passes through a device (DevS1), wherein the device (DevS1) is a continuously working device, and in the device (DevS1) the mixture of the compound of formula (II) and the compound of formula (III) is heated to temperature (TempS1), where the reaction (ReacS1) takes place,
wherein in the step (StepS2) a device (DevS2) for cooling is employed;
wherein in the step (StepS3) a device (DevS3) for back pressure regulation is employed.

16. The method according to claim 15, wherein the method further comprises
a step (StepS4), which is done after the step (StepS3), wherein in the step (StepS4) a device for separating $CO_2$ is employed.

17. The method according to claim 14, wherein
X1 and X2 are identical and are selected from the group consisting of F, Cl, Br, $C_{1-6}$ perfluoroalkyl and tolyl.

18. The method according to claim 14, wherein
R"$^{n+}$ is selected from the group consisting of H$^+$, Li$^+$, Na$^+$, K$^+$,

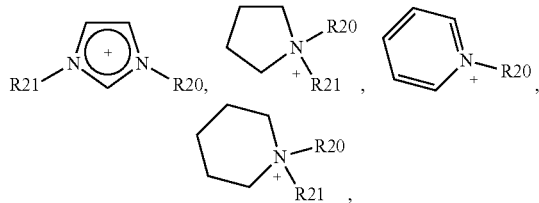

and [N(R20)(R21)(R22)R23]$^+$;

R20, R21, R22 and R23 are identical or different and R20, R21, R22 and R23 are independently from each other selected from the group consisting of H, $C_{1-8}$ alkyl, $C_{5-6}$ cycloalkyl, phenyl, benzyl, vinyl and allyl.

19. The method according to claim 15, wherein
the device (DevS1) is selected from the group consisting of a tube, a microreactor, a shell and tube heat exchanger, a plate heat exchanger and any device that can exchange heat from a reaction mixture.

20. The method according to claim 15, wherein
the device (DevS2) is selected from the group consisting of a tube, a microreactor, a shell and tube heat exchanger, a plate heat exchanger and any device that can exchange heat from a reaction mixture.

21. The method according to claim 15, wherein
the device (DevS3) is a back pressure regulating device.

22. The method according to claim 14, wherein
the temperature (TempS1) is from 190 to 280° C.

23. The method according to claim 14, wherein
the pressure (PressS1) is from 20 to 600 bar.

24. The method according to claim 15, wherein
a time (TimeS1) that the mixture is exposed to heating at the temperature (TempS1) in the device (DevS1) is from 0.5 sec to 4 h.

25. The method according to claim 14, wherein
the ratio of the molar amount of the compound of formula (III) to the molar amount of the compound of formula (II) is from 0.5:1 to 1.5:1.

26. The method according to claim 15, wherein
the reaction (ReacS1) results in a reaction mixture,
wherein in the step (StepS2) the reaction mixture from the device (DevS1) passes through a device (DevS2);
wherein in the step (StepS3) the reaction mixture from the device (DevS2) passes through a device (DevS3);
wherein the reaction mixture is cooled by the device (DevS2), the (DevS3), or a combination thereof.

27. The method according to claim 26, wherein
the reaction mixture is cooled to a temperature (TempS2) of from 0 to 150° C.

28. The method according to claim 16, wherein
in the step (StepS4) the reaction mixture from the device (DevS3) passes through a device (DevS4).

29. The method according to claim 27, wherein
the temperature (TempS2) is from 10 to 120° C.

30. The method according to claim 27, wherein
a time (TimeS2) that the mixture is cooled to the temperature (TempS2) is from 0.1 sec to 2 h.

* * * * *